United States Patent [19]

Seele et al.

[11] Patent Number: 5,062,879
[45] Date of Patent: Nov. 5, 1991

[54] 8-AZOLYLMETHYLQUINOLINES AND HERBICIDAL USE THEREOF

[75] Inventors: Rainer Seele, Fussgoenheim; Gunter Brill, Hassloch; Reiner Kober, Fussgoenheim; Thomas Saupe, Sandhausen; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 520,810

[22] Filed: May 9, 1990

[30] Foreign Application Priority Data

May 26, 1989 [DE] Fed. Rep. of Germany ....... 3917234
Aug. 1, 1989 [DE] Fed. Rep. of Germany ....... 3925422

[51] Int. Cl.$^5$ .................. C07D 401/06; A01N 43/653
[52] U.S. Cl. ........................................ 71/92; 546/167; 546/172; 546/176
[58] Field of Search ........................ 546/167, 176, 172; 71/92

[56] References Cited

U.S. PATENT DOCUMENTS 4,497,651 2/1985 Hagen et al. .............................. 71/94
4,715,889 12/1987 Hagen et al. .............................. 71/94
4,832,731 5/1989 Plath et al. ................................ 71/94

FOREIGN PATENT DOCUMENTS

86/04721 11/1986 European Pat. Off. ............ 546/167
18811/76 8/1977 South Africa .

OTHER PUBLICATIONS

*Chemical Abstracts*, vol. 89, entry 24368 (1978).

Primary Examiner—David B. Springer
Attorney, Agent, or Firm—Keil & Weinkauf

[57] ABSTRACT

8-Azolylmethylquinolines I

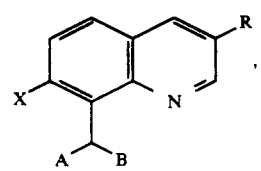

(R=H, halogen, CN, $C_1$–$C_4$-alkyl; X=halogen; A=the 1-yl radical of a 5-membered, aromatic heterocycle with 2 or 3 nitrogen atoms in the ring, which may also bear further substituents; B=Cl, Br, $C_1$–$C_4$-alkoxy, $C_1$–$C_4$-alkylthio, an amine radical which may be mono- or disubstituted, a radical $ZR^4$ where $R^4$=phenyl which may bear further substituents, and Z=oxygen, sulfur or an amine radical which may be alkylated) and the acid addition salts and metal complexes of I.

The compounds I and the salts and metal complexes thereof are suitable as herbicides.

6 Claims, No Drawings

8-AZOLYLMETHYLQUINOLINES AND HERBICIDAL USE THEREOF

The present invention relates to novel 8-azolylmethylquinolines of the formula I

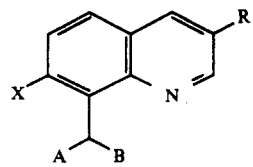

where
- R is hydrogen, halogen, cyano, $C_1$-$C_4$-alkyl or partially or completely halogenated $C_1$-$C_4$alkyl;
- X is halogen;
- A is 1,2-diazol-1-yl, 1,3-diazol-1-yl, 1,2,4-triazol-1-yl or 1,3,4-triazol-1-yl, which can carry on each of the carbon atoms one of the following substituents: halogen, mercapto, nitro, cyano, $C_1$-$C_4$-alkyl, partially or completely halogenated $C_1$-$C_4$-alkyl, $C_1$-$C_4$-alkoxy, $C_1$-$C_4$-alkylthio, $C_1$-$C_4$-alkylsulfonyl or CO—$R^1$ where $R^1$ can be $C_1$-$C_4$-alkoxy or amino;
- B is chlorine, bromine, $C_1$-$C_4$-alkoxy, $C_1$-$C_4$-alkylthio, —$NR^2R^3$ where $R^2$ and $R^3$ are hydrogen, $C_1$-$C_4$-alkyl or $C_1$-$C_4$-acyl; $ZR^4$ where $R^4$ is phenyl which can carry one nitro, cyano or phenoxy group and up to 3 of the following substituents: halogen, $C_1$-$C_4$-alkyl which can carry up to 3 halogen atoms, or $C_1$-$C_4$-alkoxy, and Z is oxygen, sulfur or —$NR^5$—where $R^5$ is hydrogen or $C_1$-$C_4$-alkyl, and the salts and metal complexes of I with those acids and metals, respectively, which do not impair the herbicidal action of I.

The present invention also relates to processes for the preparation of these compounds, to the use thereof as herbicides and to herbicidal agents which contain these compounds as active substances.

DE-A 35 24 918 and EP-B 60 429 disclose 8-azolylcarbonylquinolines, and 8-dichloromethylquinolines, respectively, as compounds with herbicidal activity.

However, the selectivity of these known herbicides with regard to weeds is only conditionally satisfactory so that the object of the present invention was to find novel compounds which have herbicidal activity and with which weeds can be controlled better than hitherto with negligible attack on crop plants.

Accordingly, we have now found the 8-azolylmethylquinolines of the formula I defined in the first paragraph.

In addition, we have found processes for the preparation of these 8-azolylmethylquinolines, and the use of these compounds as herbicides.

The compounds of the formula I contain an asymmetric carbon atom and can thus occur as enantiomers. The racemates can be resolved by conventional methods, for example by formation of a salt with an optically active acid. Both the pure enantiomers and the mixture of isomers produced in the synthesis are suitable as herbicides.

The substituents in the compounds I according to the invention have the following specific meanings:
- R is preferably hydrogen, halogen such as fluorine, chlorine, bromine and iodine, cyano, branched or unbranched $C_1$-$C_4$-alkyl, eg. methyl, ethyl, propyl, i-propyl, trichloromethyl and branched or unbranched, partially or completely halogenated $C_1$-$C_4$-alkyl, e.g. trifluoromethyl; chlorine and bromine are particularly preferred;
- X is halogen, particularly fluorine, chlorine and bromine;
- A is 1,2-diazol-1-yl, 1,3-diazol-1-yl, 1,2,4-triazol-1-yl or 1,3,4-triazol-1-yl, which can carry on each of the carbon atoms one of the following groups: halogen such as fluorine, chlorine and bromine, mercapto, nitro, cyano, $C_1$-$C_4$-alkyl such as methyl, partially or completely halogenated $C_1$-$C_4$-alkyl, $C_1$-$C_4$-alkoxy such as methoxy, $C_1$-$C_4$-alkylthio such as methylthio, $C_1$-$C_4$-alkylsulfonyl, $C_1$-$C_4$-alkoxycarbonyl or aminocarbonyl; particularly preferred are pyrazolyl, imidazolyl, 2-methylimidazolyl, 4-COOCH$_3$-imidazolyl, 4-CONH$_2$-imidazolyl, 5-nitromidazolul, 4,5-dichloroimidazolyl, 1,2,4-triazolyl, 1,3,4-triazolyl, 5-mercapto-1,2,4-triazolyl and 5-mercapto-1,3,4-triazolyl;
- B is chlorine and bromine, branched or unbranched $C_1$-$C_4$-alkoxy, particularly methoxy, ethoxy and i-propoxy, phenoxy or substituted phenoxy, especially 2-halophenoxy, 2-fluorophenoxy, 4-halophenoxy, 4-chlorophenoxy, 2,4-dihalophenoxy, such as 2,4-dichlorophenoxy, 4-trihaloalkylphenoxy, such as 4-trifluoromethylphenoxy, 4-alkoxyphenoxy, such as 4-methoxyphenoxy and phenoxyphenoxy, $C_1$-$C_4$-alkylthio, particularly methylthio and ethylthio, phenylthio or substituted phenylthio, particularly 4-halophenylthio, such as 4-chlorophenylthio, amino, $C_1$-$C_4$-alkylamino, particularly methylamino and ethylamino, di-($C_1$-$C_4$-alkyl)amino such as dimethylamino, $C_1$-$C_4$-acylamino or N-($C_1$-$C_4$-acyl)-N-($C_1$-$C_4$-alkyl)amino or phenylamino or phenylalkylamino, particularly phenylamino.

Suitable compounds are listed in the examples in Table I.

Particularly suitable compounds are those in which R and X are, independently of one another, halogen, especially chlorine, A is 1,2,4-triazol-1-yl or 1,3,4-triazol-1-yl, and B is chlorine or bromine.

Suitable acid addition salts are salts of those acids which do not impair the herbicidal action of I, eg. the hydrochlorides and hydrobromides, sulfates, nitrates, phosphates, oxalates or dodecylbenzenesulfonates.

Suitable metal complexes are the complexes of copper, zinc, tin, manganese, iron, cobalt or nickel. The complexes are preferably prepared from the free bases I and salts of mineral acids, for example the chlorides or sulfates of the metals.

If B in the compounds I according to the invention is chlorine or bromine, they are prepared in a very advantageous manner by a method similar to that described by H. Matsumoto et al. (Tetrahedron Letters 52 (1979) 5011) by reacting the azoles AH with an 8-formylquinoline II and an inorganic acid halide (YHal$_2$) as shown in the following equation:

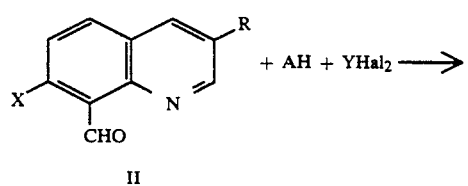 + AH + YHal₂ ⟶

II

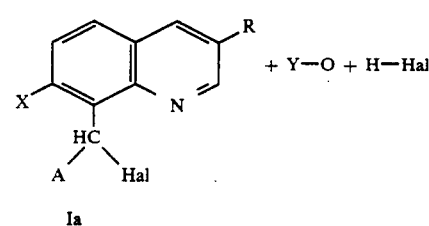 + Y=O + H—Hal

Ia

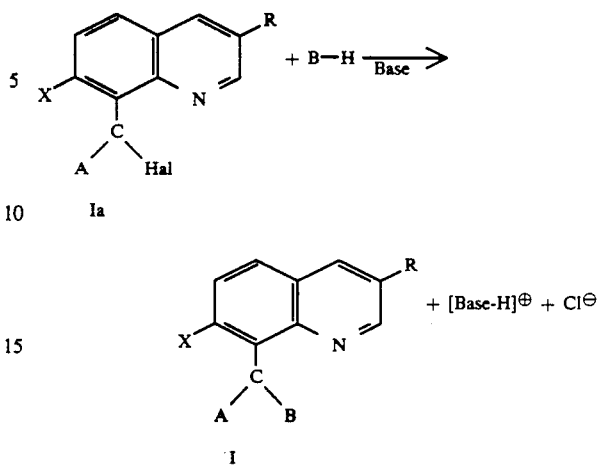

The inorganic acid halides (YHal₂) are halogenating agents such as phosphorus oxychloride, thiophosgene and, preferably, phosgene and thionyl chloride and bromide.

The starting compounds II are known or can be obtained in a conventional manner (cf. EP-B 60 429), eg. by oxidation of substituted 8-methylquinolines of the formula III

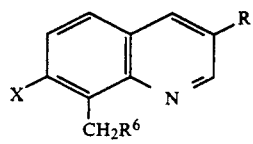     (III)

where $R^6$ is chlorine, bromine, methoxy or acetoxy.

Oxidizing agents which can be used are inorganic oxidizing acids, metal oxides such as chromium trioxide or nitroalkanes such as 2-nitropropane.

The acid halide is preferably employed in at least the equimolar amount, in particular from 1 to 2 times the amount, based on the formylquinoline II. The azole component AH is employed in twice, preferably 5-6 times, the molar amount based on the acid chloride or bromide.

The reaction is preferably carried out at from −30° to +100° C., particularly preferably at from 0° to 20° C., in the presence of a solvent.

Examples of preferred solvents are nitriles such as acetonitrile, ethers such as tetrahydrofuran, diethyl ether or dioxane. Hydrocarbons and chlorohydrocarbons are particularly preferred, such as hexane, benzene, toluene, methylene chloride, tetrachloromethane or mixtures of the said solvents.

The reaction is generally carried out under atmospheric pressure, unless an elevated pressure, up to about 5 bar, is advisable because of volatile reactants.

Since the acid halides and the intermediates are sensitive to hydrolysis, the reaction is preferably carried out with exclusion of moisture, particularly preferably under a protective gas atmosphere.

The compounds I in which B is not chlorine or bromine can be prepared particularly advantageously from the chlorine or bromine compounds Ia by reacting them with a compound H-B and a base.

The component B-H is advantageously employed in stoichiometric amounts, preferably in an excess of about 20%, based on the 8-azolylhalomethylquinolines Ia.

The reaction is advantageously carried out with the addition of an organic or inorganic base and/or of a reaction accelerator in the presence of a solvent.

The amounts of base and reaction accelerator can vary depending on the compound employed. A small excess (up to about 10%) of base relative to the 8-azolylquinoline Ia is advantageously used.

Examples of suitable bases are alkali metal hydroxides such as lithium, sodium or potassium hydroxide, alkali metal carbonates or bicarbonates such as sodium or potassium carbonate or sodium or potassium bicarbonate, alkali metal amides such as those of sodium or potassium, and the organic bases pyridine, 4-dialkylaminopyridine, dialkylamines and dialkylanilines or, preferably, the alkali metal salt of the component B-H.

It is also possible to use the component A-H employed for the preparation of the 8-azolylmethylquinolines Ia as base.

The reaction accelerator is preferably added to the reaction mixture in catalytic amounts.

Examples of reaction accelerators which can be used are metal halides, preferably sodium iodide or potassium iodide, quaternary ammonium salts such as tetraalkylammonium halides or bisulfates, preferably tetrabutylammonium chloride, bromide or iodide, aryltrialkylammonium halides such as benzyltriethylammonium chloride or bromide and crown ethers such as 12-crown-4, 15-crown-5, benzo-15-crown-5, dibenzo-18-crown-6or dicyclohexano-18-crown-6.

Solvents which are preferably used are ketones such as acetone, methyl ethyl ketone or cyclohexanone, nitriles such as acetonitrile or propionitrile, alcohols such as methanol, ethanol, i-propanol, n-butanol, glycols, esters such as methyl acetate, ethyl acetate or butyl acetate, ethers such as tetrahydrofuran, diethyl ether, dimethoxyethane, dioxane or diisopropyl ether, amides such as dimethylformamide, dimethylacetamide or N-methylpyrrolidone, and dimethyl sulfoxide, sulfolane or mixtures of the said solvents.

The reaction is advantageously carried out at from 0° to 180° C., preferably at the boiling point of the solvent used.

The statements concerning the pressure for the preparation of the compound Ia apply here.

The processes according to the invention for the preparation of substituted 8-azolylmethylquinolines can be carried out continuously or batchwise.

The compounds I and the defined salts and complexes thereof are suitable as herbicides.

The 8-azolylmethylquinolines, and herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetate, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, and preferably from 95 to 100, % (according to the NMR spectrum).

Examples of formulations are as follows:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 5 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 21 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 24 is intimately mixed with 97 parts by weight of particulate kaolin. A dust is obtained containing 3% by weight of the active ingredient.

VII. 30 parts by weight of compound no. 27 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 33 is mixed with 10 parts by weight of the sodium salt of a phenolsulfonic acid-urea-formaldehyde condensate, 2 parts by weight of silica gel and 48 parts by weight of water to give a stable aqueous dispersion which can be further diluted.

IX. 20 parts by weight of compound no. 47 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

X. 10 parts by weight of compound no. 48, 4 parts by weight of the sodium salt of diisobutylnaphthalene-α-sulfonic acid, 20 parts by weight of the sodium salt of a ligninsulfonic acid obtained from a sulfite waste liquor, 38 parts by weight of silica gel and 38 parts by weight of kaolin are triturated in a hammer mill. By finely distributing the mixture in 100,000 parts by weight of water a spray liquor is obtained cotaining 0.1 wt % of the active ingredient.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 2.0, kg of active ingredient per hectare.

In view of the numerous application methods possible, the compounds according to the invention, or the agents containing them, may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the 8-azolylmethylquinolines I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-diones, quinolinecarboxylic acids, (hetero)-aryloxyphenoxypropionic acid derivatives and their salts, esters, amides, etc.

It may also be useful to apply the herbicidal compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

PREPARATION EXAMPLES

EXAMPLE 1

3,7-Dichloro-8-[(1,2,4-triazol-1-yl)chloromethyl]quinoline

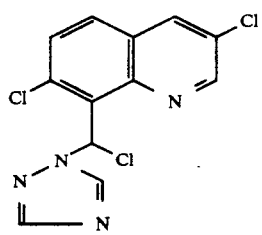

To a solution of 29.7 g (0.43 mol) of triazole in 150 ml of methylene chloride at 0° C. under a nitrogen atmosphere were added 12.8 g (0.11 mol) of thionyl chloride and, after stirring at 25° C. for 30 minutes, 16.3 g ($7.2 \times 10^{-2}$ mol) of 3,7-dichloroquinoline-8-carbaldehyde.

After reaction at 25° C. for 12 hours, 100 ml of water were added, and the aqueous phase was separated off and extracted twice with methylene chloride. The combined organic phases were then worked up as usual to give the 8-azolylchloromethylquinoline derivative. Recrystallization from isopropanol yielded 19 g of product. Yield: 84%; melting point 140°-146° C.

EXAMPLE 2

3,7-Dichloro-8-[(1,2,4-triazol-1-yl)methoxymethyl]-quinoline

A solution of 5 g ($1.6 \times 10^{-2}$ mol) of 3,7-dichloro-8-[(1,2,4-triazol-1-yl)chloromethyl]quinoline (Example 1), 2.2 g ($4.1 \times 10^{-2}$ mol) of sodium methylate and a spatula tip of potassium iodide in 100 ml of methanol was refluxed for 5 hours and then 100 ml of water were added. After extraction with methyl tert-butyl ether, the organic phase was washed and worked up as usual. Yield: 4.5 g (91%); melting point 156°-158° C.

The compounds listed in Table 1 were prepared in a similar manner to Examples 1 and 2.

TABLE 1

Novel herbicidal 8-azolylmethylquinolines

| Ex. | R | X | A | B | mp. [°C.] | Prep. similar to Ex. |
|---|---|---|---|---|---|---|
| 3 | Cl | Cl | 1,2,4-triazolyl | Br | 155 | 1 |
| 4 | Cl | Cl | 1,2,4-triazolyl | OC$_2$H$_5$ | | 2 |
| 5 | Cl | Cl | 1,2,4-triazolyl | O-iso-C$_3$H$_7$ | 119–125 | 2 |
| 6 | Cl | Cl | 1,2,4-triazolyl | SCH$_3$ | | 2 |
| 7 | Cl | Cl | 1,2,4-triazolyl | NHCH$_3$ | | 2 |
| 8 | Cl | Cl | 1,2,4-triazolyl | S—C$_6$H$_5$ | | 2 |
| 9 | Cl | Cl | 1,2,4-triazolyl | NH—C$_6$H$_5$ | | 2 |
| 10 | Cl | Cl | 1,2,4-triazolyl | O—C$_6$H$_5$ | | 2 |
| 11 | Cl | Cl | 1,2,4-triazolyl | O—C$_6$H$_4$—Cl (4-Cl) | | 2 |
| 12 | Cl | Cl | 1,2,4-triazolyl | O—C$_6$H$_3$—Cl$_2$ (2,4-Cl$_2$) | | 2 |
| 13 | Cl | Cl | 1,2,4-triazolyl | O—C$_6$H$_4$—CF$_3$ (4-CF$_3$) | | 2 |
| 14 | Cl | Cl | pyrazolyl | Cl | | 1 |
| 15 | Cl | Cl | pyrazolyl | Br | | 1 |
| 16 | Cl | Cl | pyrazolyl | OCH$_3$ | | 2 |
| 17 | Cl | Cl | imidazolyl | Cl | | 1 |
| 18 | Cl | Cl | imidazolyl | OCH$_3$ | | 2 |
| 19 | Cl | Cl | 5-nitro-imidazolyl | Cl | | 1 |

TABLE 1-continued

Novel herbicidal 8-azolylmethylquinolines

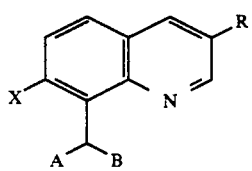

| Ex. | R | X | A | B | mp. [°C.] | Prep. similar to Ex. |
|---|---|---|---|---|---|---|
| 20 | Cl | Cl | 5-nitro-imidazolyl | OC$_2$H$_5$ | | 2 |
| 21 | Cl | Cl | 4,5-dichloroimidazolyl | Cl | resin | 1 |
| 22 | Cl | Cl | 4,5-dichloroimidazolyl | OCH$_3$ | | 2 |
| 23 | Cl | Cl | 2-methylimidazolyl | Cl | | 1 |
| 24 | Cl | Cl | 4-cyano-imidazolyl | Cl | resin | 1 |
| 25 | Cl | Cl | 4-cyano-imidazolyl | OCH$_3$ | | 2 |
| 26 | Cl | Cl | 4-cyano-imidazolyl | SCH$_3$ | | 2 |
| 27 | Cl | Cl | 4-CONH$_2$-imidazolyl | Cl | 174–180 | 1 |
| 28 | Cl | Cl | 4-CONH$_2$-imidazolyl | OCH$_3$ | | 2 |
| 29 | Cl | CL | 4-CONH$_2$-imidazolyl | SCH$_3$ | | 2 |
| 30 | Cl | Cl | 4-CONH$_2$-imidazolyl | O—C$_6$H$_5$ | | 2 |
| 31 | Cl | Cl | 4-CONH$_2$-imidazolyl | NH—C$_6$H$_5$ | | 2 |
| 32 | Cl | Cl | 4-CONH$_2$-imidazolyl | S—C$_6$H$_5$ | | 2 |
| 33 | Cl | Cl | 4-COOCH$_3$-imidazolyl | Cl | resin | 1 |
| 34 | Cl | Cl | 4-COOCH$_3$-imidazolyl | OCH$_3$ | | 2 |
| 35 | Cl | Cl | 4-COOCH$_3$-imidazolyl | OC$_2$H$_5$ | | 2 |
| 36 | Cl | Cl | 4-COOCH$_3$-imidazolyl | O—C$_6$H$_5$ | | 2 |
| 37 | Cl | Cl | 4-COOCH$_3$-imidazolyl | S—C$_6$H$_5$ | | 2 |
| 38 | Cl | Cl | 5-mercapto-1,2,4-triazolyl | Cl | | 1 |
| 39 | Cl | Cl | 5-mercapto-1,2,4-triazolyl | OCH$_3$ | | 2 |
| 40 | F | Cl | 1,2,4-triazolyl | Cl | | 1 |
| 41 | F | Cl | 1,2,4-triazolyl | OCH$_3$ | | 2 |
| 42 | F | Cl | 1,2,4-triazolyl | Br | | 1 |
| 43 | Br | Cl | 1,2,4-triazolyl | Cl | | 1 |
| 44 | Cl | F | 1,2,4-triazolyl | Cl | | 1 |
| 45 | Cl | F | 1,2,4-triazolyl | OCH$_3$ | | 2 |
| 46 | Cl | Br | 1,2,4-triazolyl | Cl | | 1 |
| 47 | CH$_3$ | Cl | 1,2,4-triazolyl | Cl | 148–155 | 1 |
| 48 | CH$_3$ | Cl | 1,2,4-triazolyl | OCH$_3$ | 151–154 | 2 |
| 49 | CH$_3$ | Cl | 1,2,4-triazolyl | Br | | 1 |
| 50 | CH$_3$ | Cl | 1,2,4-triazolyl | OC$_2$H$_5$ | | 2 |
| 51 | CH$_3$ | Cl | 1,2,4-triazolyl | SCH$_3$ | | 2 |
| 52 | CH$_3$ | Cl | 1,2,4-triazolyl | O—C$_6$H$_5$ | | 2 |
| 53 | CH$_3$ | Cl | 1,2,4-triazolyl | S—C$_6$H$_5$ | | 2 |
| 54 | CH$_3$ | Cl | 1,2,4-triazolyl | NH—C$_6$H$_5$ | | 2 |
| 55 | CH$_3$ | Cl | 1,2,4-triazolyl | O—C$_6$H$_4$—OCH$_3$ (para) | | 2 |
| 56 | CH$_3$ | Cl | 1,2,4-triazolyl | O—C$_6$H$_4$—F (ortho) | | 2 |
| 57 | CH$_3$ | Cl | imidazolyl | Cl | | 1 |
| 58 | CH$_3$ | Cl | imidazolyl | OCH$_3$ | | 2 |
| 59 | CH$_3$ | Cl | pyrazolyl | Cl | | 1 |
| 60 | CH$_3$ | Cl | pyrazolyl | Br | | 1 |
| 61 | CH$_3$ | Cl | pyrazolyl | OCH$_3$ | | 2 |
| 62 | CH$_3$ | Cl | pyrazolyl | O—C$_6$H$_5$ | | 2 |
| 63 | CH$_3$ | Cl | pyrazolyl | S—C$_6$H$_4$—Cl (para) | | 2 |
| 64 | CH$_3$ | Cl | 4-CONH$_2$-imidazolyl | Cl | | 1 |
| 65 | CH$_3$ | Cl | 4-CONH$_2$-imidazolyl | OCH$_3$ | | 2 |
| 66 | H | Cl | 1,2,4-triazolyl | Cl | | 1 |
| 67 | H | Cl | 1,2,4-triazolyl | OCH$_3$ | | 2 |
| 68 | CF$_3$ | Cl | 1,2,4-triazolyl | Cl | | 1 |
| 69 | CF$_3$ | Cl | imidazolyl | Cl | | 1 |
| 70 | CF$_3$ | Cl | imidazolyl | OCH$_3$ | | 2 |
| 71 | CF$_3$ | Cl | imidazolyl | OC$_6$H$_5$ | | 2 |

TABLE 1-continued

Novel herbicidal 8-azolylmethylquinolines

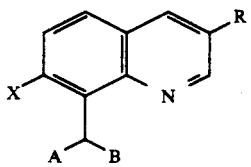

| Ex. | R | X | A | B | mp. [°C.] | Prep. similar to Ex. |
|---|---|---|---|---|---|---|
| 72 | CN | Cl | 1,2,4-triazolyl | Cl | | 1 |
| 73 | CN | Cl | 1,2,4-triazolyl | OCH$_3$ | | 2 |
| 74 | CN | Cl | pyrazolyl | Cl | | 1 |
| 75 | CN | Cl | pyrazolyl | OCH$_3$ | | 2 |

USE EXAMPLES

The herbicidal action of the 8-azolylmethylquinolines of the formula I is illustrated in the following greenhouse experiments.

The vessels employed were plastic flowerpots having a volume of 300 cm$^3$ and filled with a sandy loam containing about 3.0% humus. The seeds of the test plants were sown separately, according to species.

In the preemergence treatment, the active ingredients were emulsified or suspended in water and sprayed through finely distributing nozzles. The vessels were lightly sprinkler-irrigated to induce germination and growth, and then covered with transparent plastic hoods until the plants had taken root. This cover caused uniform germination of the test plants insofar as this was not impaired by the active ingredients.

For the postemergence treatment, the plants were grown, depending on growth form, to a height of 3 to 15 cm before being treated with the active ingredients, which were suspended or emulsified in water.

The application rate for pre- and postemergence treatment was 1.0 kg/ha.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the experiments were Cassia tora, Galium aparine, Solanum nigrum and Zea mays.

Compounds nos. 1 and 3, applied both pre- and postemergence, combated broadleaved plants very well and were well tolerated by the crop plant Indian corn (tested preemergence).

We claim:

1. A substituted 8-azolylmethylquinoline of the formula I

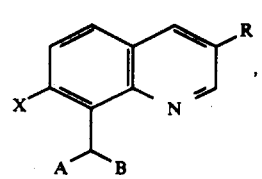

where R is hydrogen, halogen, cyano or C$_1$–C$_4$-alkyl or partially or completely halogenated C$_1$–C$_4$-alkyl;

X is halogen;

A is; pyrazol-1-yl, imidazol-1-yl, 1,2,4-triazol-1-yl, 1,3,4-triazol-1-yl, 5-mercapto-1,2,4-triazol-1-yl, 5-mercapto-1,3,4-triazol-1-yl or is imidazol-1-yl which at each carbon atom can bear one of the following substituents: halogen, thiol, nitro, cyano, C$_1$–C$_4$-alkyl, partially or completely halogenated C$_1$–C$_4$-alkyl, C$_1$–C$_4$-alkoxy, C$_1$–C$_4$-alkylthio, C$_1$–C$_4$-alkylsulfonyl, or a group CO—R$^1$, R$^1$ denoting C$_1$–C$_4$-alkoxy or amino;

B is chlorine, bromine, C$_1$–C$_4$-alkoxy, C$_1$–C$_4$-alkylthio or —(NR$^2$R$^3$), R$^2$ and R$^3$ denoting hydrogen, C$_1$–C$_4$-alkyl or C$_1$–C$_4$-acyl; ZR$^4$, R$^4$ denoting phenyl which may bear a nitro, cyano or phenoxy group and up to 3 of the following substituents: halogen, C$_1$–C$_4$-alkyl which may bear up to 3 halogen atoms, or C$_1$–C$_4$-alkoxy, and Z is oxygen, sulfur or —(NR$^5$)—, R$^5$ being hydrogen or C$_1$–C$_4$-alkyl, and the salts and metal complexes of I with acids or metals which do not impair the herbicidal action of I.

2. A substituted 8-azolylmethylquinoline of the formula I as set forth in claim 1, R and X denotes halogen, A denotes triazol-1-yl and B denotes chlorine or bromine.

3. A substituted 8-azolylmethylquinoline of the formula I as set forth in claim 1, wherein A is pyrazol-1-yl, imidazol-1-yl, 2-methylimidazol-1-yl, 4-COOCH$_3$-imidazol-1-yl, 4-CONH$_2$-imidazol-1-yl, 5-nitroimidazol-1-yl, 4,5-dichloroimidazol-1-yl, 1,2,4-triazol-1-yl, 1,3,4-triazol-1-yl, 5-mercapto-1,2,4-triazol-1-yl or 5-mercapto-1,3,4-triazol-1-yl.

4. A substituted 8-azolylquinoline of the formula I as set forth in claim 1, wherein R and X are each chlorine, A is triazol-1-yl and B is methoxy.

5. A herbicidal composition containing a herbicidally effective amount of an 8-azolylmethylquinoline of the formula I, or an acid addition salt or metal complex thereof as set forth in claim 1, and a solid or liquid carrier.

6. A process for combating the growth of unwanted plants, wherein a herbicidally effective amount of a substituted 8-azolylmethylquinoline of the formula I, or an acid addition salt or metal complex thereof as set forth in claim 1 is allowed to act on plants, their habitat or seed.

* * * * *

UNITED STATES PATENT AND TRADEMARK OFFICE
CERTIFICATE OF CORRECTION

PATENT NO. : 5,062,879

DATED : November 5, 1991

INVENTOR(S) : Rainer SEELE et al.

It is certified that error appears in the above-identified patent and that said Letters Patent is hereby corrected as shown below:

On the title page: In the Abstract,

That part reading "(R=H, halogen, CN, $C_1-C_4$-alkyl;" should read --(R=H, halogen, CN, $C_1-C_4$-alkyl or haloalkyl--

Signed and Sealed this

Sixth Day of April, 1993

*Attest:*

STEPHEN G. KUNIN

*Attesting Officer*  *Acting Commissioner of Patents and Trademarks*